United States Patent
Deco et al.

(10) Patent No.: US 6,266,624 B1
(45) Date of Patent: Jul. 24, 2001

(54) METHOD CONDUCTED IN A COMPUTER FOR CLASSIFICATION OF A TIME SERIES HAVING A PRESCRIBABLE NUMBER OF SAMPLES

(75) Inventors: Gustavo Deco, München; Bernd Schürmann, Haimhausen, both of (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/142,265

(22) PCT Filed: Mar. 5, 1997

(86) PCT No.: PCT/DE97/00416

§ 371 Date: Sep. 3, 1998

§ 102(e) Date: Sep. 3, 1998

(87) PCT Pub. No.: WO97/35267

PCT Pub. Date: Sep. 25, 1997

(30) Foreign Application Priority Data

Mar. 19, 1996 (DE) ............................................. 196 10 847

(51) Int. Cl.[7] ................................................... G06F 17/00
(52) U.S. Cl. .................................. 702/73; 702/79; 128/91
(58) Field of Search ........................... 600/515; 128/901; 702/73, 79

(56) References Cited

FOREIGN PATENT DOCUMENTS

WO009725676 * 7/1997 (JP) .............................. G06F/17/00
WO009733238 * 2/1997 (WO) ............................ G06F/17/18

OTHER PUBLICATIONS

"Komolexitätsanalyse in der Kardiologie," Morfill, Physikalische Blätter, vol. 50, No. 2, pp. 156–160, (1994.

"Entropy, Transinformation and Word Distribution of Information–Carrying Sequences," Ebeling et al., International Journal of Bifurcation and Chaos, vol. 5, No. 1, pp. 51–61, (1995).

Estimation Functions of Probability Distributions From a Finite Set of Samples, Wolpert et al., Physical Review E, vol. 52, No. 6, pp. 6841–6854, (Dec. 1995).

LICOX, GMS, Gesellschaft für Medizinische Sondentechnik mbH, Advanced Tissue Monitoring, no date.

"Time Series Analysis of Complex Dynamics in Physiology and Medicine," Glass et al., Medical Progress Through Technology, vol. 19, No. 3, pp. 115–128 (1993).

* cited by examiner

Primary Examiner—Kamini Shah
(74) Attorney, Agent, or Firm—Schiff Hardin & Waite

(57) ABSTRACT

A method for determining conditioned entropies for a prescribable plurality of future sampling times for a set of samples based upon an information flow. A classification of a time series is implemented on the basis of the information flow. The information flow reflects nonlinear correlations between the samples. A classification is thus possible between those time series whose samples are non-linearly correlated and those time series whose samples are stochastically independant.

8 Claims, 5 Drawing Sheets

METHOD CONDUCTED IN A COMPUTER FOR CLASSIFICATION OF A TIME SERIES HAVING A PRESCRIBABLE NUMBER OF SAMPLES

BACKGROUND OF THE INVENTION

1. Field of the Invention

The present invention is directed to computerized method, i.e., a method conducted in a computer, for classification of a time series having a prescribable number of samples, such as an electrical signal.

2. Description of the Prior Art

In many technical fields wherein it is of interest to draw conclusions about the future behavior of the time series from measured time series. The prediction of the future "behavior" of the time series ensues given the assumption that the time series comprises non-linear correlations between the samples of the time series.

This problem also obtains to considerable significance in various medical fields, for example in cardiology. Specifically in the problem area of sudden cardiac death, it can be vital to recognize early warning signs of sudden cardiac death in order to initiate counter-measures against the occurrence of sudden cardiac death as early as possible.

It is known that a time series of an electrocardiogram that is not correlated describes a heart that is not at risk with respect to sudden cardiac death. A heart at risk with respect to sudden cardiac death is described by a time series of the electrocardiogram that comprises non-linear correlations between the samples of the time series (G. Morfill, "Komplexitätsanalyse in der Kardiologie, Physikalische Blätter," Vol. 50, No. 2, pp. 156–160, (1994)). It is also known from this Morfill article to determine time series of an electrocardiogram that describe hearts that are at risk with respect to sudden cardiac death from the graphic phase space presentation (Fourier transformation) of two successive heartbeats.

The method disclosed in this Morfill article exhibits all of the disadvantages that are typical of empirical methods. In particular, the error susceptibility of graphic interpretations by a human, the problem of setting a threshold from which a time series is classified as at risk, as well as imprecisions in the presentation of the Fourier transform on the picture screen are considered disadvantageous in the known method.

Further, methods for determining stochastic, conditioned entropies are known from W. Ebeling et al., "Entropy, Transinformation and Word Distribution of Information-Carrying Sequences," International Journal of Bifurcation and Chaos, Vol. 5, No. 1, pp. 51–61, (1995) and D. Wolpert et al., "Estimation Functions of Probability Distributions from a Finite Set of Samples," Physical Review E, Vol. 52, No. 6, pp. 6841–6854, (December 1995).

LICOX, GMS, Gesellschaft für Medizinische Sondentechnik mbH, Advanced Tissue Monitoring discloses a method with which the time curve of the local oxygen voltage of the brain (tipO2) can be determined.

German OS 39 12 028 discloses a method and an arrangement for comparing wave shapes of time-variable signals.

SUMMARY OF THE INVENTION

An object of the present invention is to provide a method in order to quickly and dependably classify a time series that contains a prescribable number of samples with the assistance of a computer.

The above object is achieved in a method conducted in a computer for classification of a time series that contains a prescribable number of samples, such as an electrical signal, by determining, in the computer, conditioned entropies for the prescribable number of samples contained in the time series, with at least one information flow for a prescribable number of future sampling times being determined in the computer from the conditioned entropies, and wherein a classification of the time series is implemented in the computer on the basis of the information flow.

In the inventive method, conditioned entropies are determined for a prescribable plurality of samples. An information flow for a prescribable plurality of future sampling points with reference whereto the time series is classified is determined from the conditioned entropies.

It is possible to speed up the classification with the method according to patent claim 5 since only a binary classification has to be implemented on the basis of the shape of the graph of the information flow. The classification of the time series into a first time series type and into a second time series type can be very simply implemented since the first time series type is classified when the graph of the information flow exhibits an approximately curved shape.

It is also advantageous to utilize the method for a time series that is made available by a measured electrocardiogram signal (ECG). A classification of the time series into an electrocardiogram signal (ECG) that describes a heart at risk with respect to sudden cardiac death as well as into an electrocardiogram signal (ECG) of a heart not at risk is possible with the determination of stochastic correlations between the samples of the time series. As a result, it is possible to recognize a risk early and to initiate a treatment against sudden cardiac death.

DESCRIPTION OF THE PREFERRED EMBODIMENTS

Figure 1:
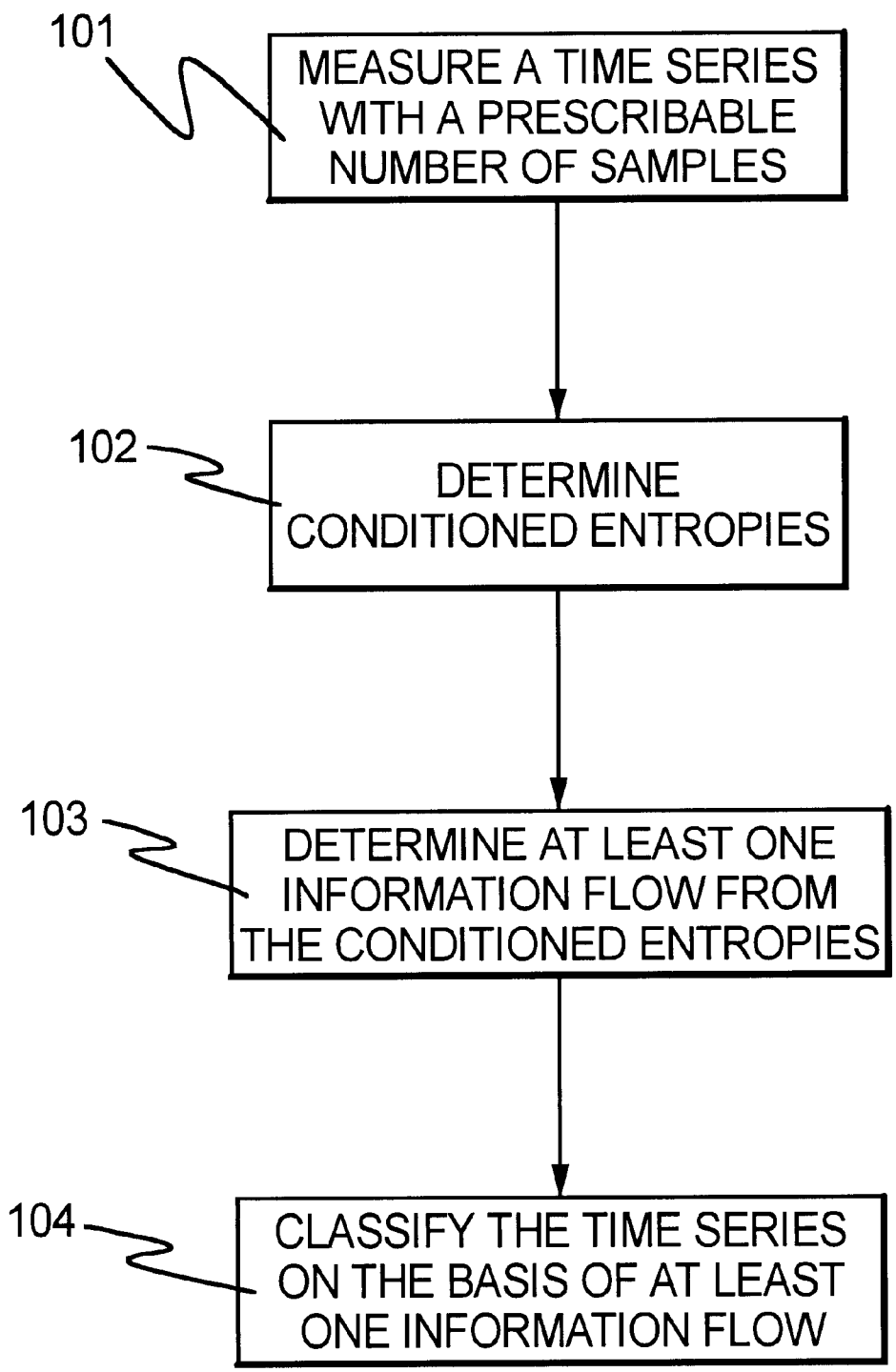
FIG. 1 is a flowchart describing the basic steps of the inventive method.

FIG. 1 shows that the time series that comprises a prescribable plurality of samples is measured 101 in a first step of the inventive method. The measurement ensues with a measuring instrument MG that measures both analog as well as digital signals and supplies them to a computer R (see FIG. 4). The computer R determines 102 conditioned entropies $H(n|n-1 \ldots 1)$ for the individual samples of the time series. Various procedures are known The aforementioned Ebeling et al. and Wolpert et al. articles for the determination of the conditioned entropies $H(n|n-1 \ldots 1)$. For example, the following definition is employed in the framework of this document for the conditioned entropies H(n|n−1 . . . 1), which, however, does not limit the possibility of employing other definitions in the framework of the inventive method:

$$H(n|n-1\ldots 1) \sum_{i=1}^{k_n-1} \sum_{j=1}^{m} p(j,i) \cdot \log(p(j|i)) \quad (1)$$

whereby

H(n|n−1 . . . 1) respectively references the conditioned entropies, n references a length of a sequence of samples of the time series taken into consideration $k_n$ ($k_n=m^n$) references a number of different sequences of considered samples having the length n, m references a number of values that the samples can assume, p(j,i) references the union probabilities, and p(j|i) references conditioned probabilities.

It is provided in the inventive method to determine the conditioned entropies H(n|n−1 . . . 1) for the prescribable number of samples that the time series comprises. However, it is likewise provided to not determine some conditioned entropies H(n|n−1 . . . 1) and to thus not take the corresponding samples into consideration. This corresponds to a reduction of the number of samples. The number of samples of the time is series taken into consideration directly reflects the precision of the inventive method with respect to the classification of the time series.

Their number of values m that the samples can assume is prescribable. The values can but need not be distributed over constant intervals.

Different possible values of samples can likewise be prescribed for different classifications. A set of prescribable values of the number m is referred to below as a partition β. The partition β thus references a set of disjunctive intervals $B_i$, i.e.

$$\beta = \{B_i\}_{i=1}^{m}, \bigcup_{i=1}^{m} B_i = A \wedge B_i \cap B_j = \phi \text{ for } i \neq. \quad (2)$$

i and j thereby reference a first running index and a second running index.

$$H^\beta(n) = -\sum_{i=1}^{k_n} p^{i,\beta}(n) \cdot \log(p^{i,\beta}(n)) \quad (3)$$

thus derives as a block entropy.

$p^{i,\beta}(n)$ thereby references the probability of the occurrence of a sample that exhibits the sample i for the partition β given a sequence of the length n.

An entropy for a prescribable number of future sampling times p is established by $$H^\beta(n,p) = -\sum_{i=1}^{k_n} \sum_{j=1}^{m} p^{i,j,\beta}(n,p) \cdot \log(p^{i,j,\beta}(n,p)) \quad (4)$$

$p^{i,j,\beta}(n,p)$ thereby references the union probability of the occurrence of a sample i for the sequence having the length n and the occurrence of the sample j at a point in time that is ahead of the prescribable number of future sampling times in the framework of the partition β. With the respective pre-condition that the chronologically directly preceding sampling time is known, a conditioned entropy is referenced Hβ ((n+1)|n . . . 1).

An information flow for the prescribable number of future sampling times p for a specific partition β is formed according to the following rule:

$$I_p^\beta = \lim_{n \to \infty} I^\beta(n+p, n+n+1|n\ldots 1|). \quad (6)$$

$I^\beta(n+p,n+1|\ldots 1)$ thereby derives from $I^\beta(n+p,n+1|\ldots 1) = H^\beta(n+p|n\ldots 1) + H^\beta(n+p|n+1\ldots 1).$ The partition β is defined as an infinitesimal partitioning, so that ε=diameter (β)→0 is valid, whereby a respectively largest cell length is referenced with diameter (β).

The information flow $I_p^\beta$ in the inventive method for a prescribable number of future sampling times p is thus formed dependent on a prescribable number of past samples n that the time series comprises.

At least one information flow $I_p^\beta$ is determined from the conditioned entropies in a third step 103.

Figure 5:
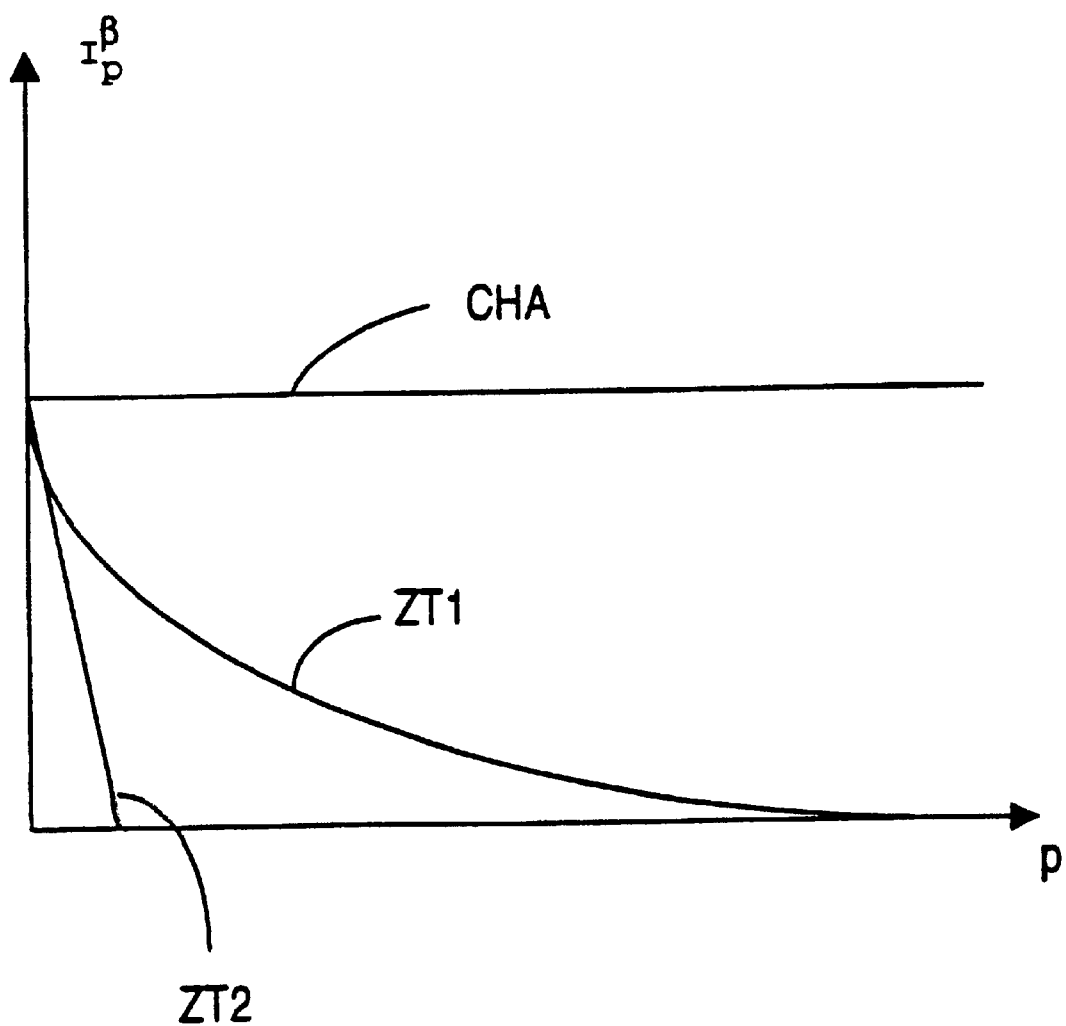
FIG. 5 is a graph showing information flow for future values for a chaotic time series, determined in accordance with the invention, as well as a time series having non-linear correlations between its samples, as well as a time series having samples which are stochastically independent of one another.

A graph of the function of the information flow $I_p^\beta$ exhibits different characteristic shapes for different time series (see FIG. 5).

In an ideal approximation, the information flow $I_p^\beta$ of a partition R exhibits a constant, horizontal course over the samples p for a chaotic time series CHA.

A monotonously falling, parabola-like curved function ZT1 derives qualitatively for the information flow $I_p^\beta$ of a time series whose samples exhibit non-linear correlations. This corresponds to a first time series type ZT1. When, however, the samples exhibit no correlations whatsoever with one another, then a steep, approximately linearly falling graph of the information flow $I_p^\beta$ for future samples is qualitatively established. This is clear on the basis of the consideration that, given non-existent correlation, future samples cannot be predicted in any way whatsoever and, thus, no information whatsoever about future samples are present. This is simply not the case for a time series whose samples exhibit non-linear correlations.

In a last step 104, a classification is implemented on the basis of the information flow $I_p^\beta$. This classification can be of a different nature dependent on the area of employment.

A very simple classification that, however, proves to be an advantageous and adequate development of the method for some types of times series is comprised in a "binary" classification.

Figure 2:
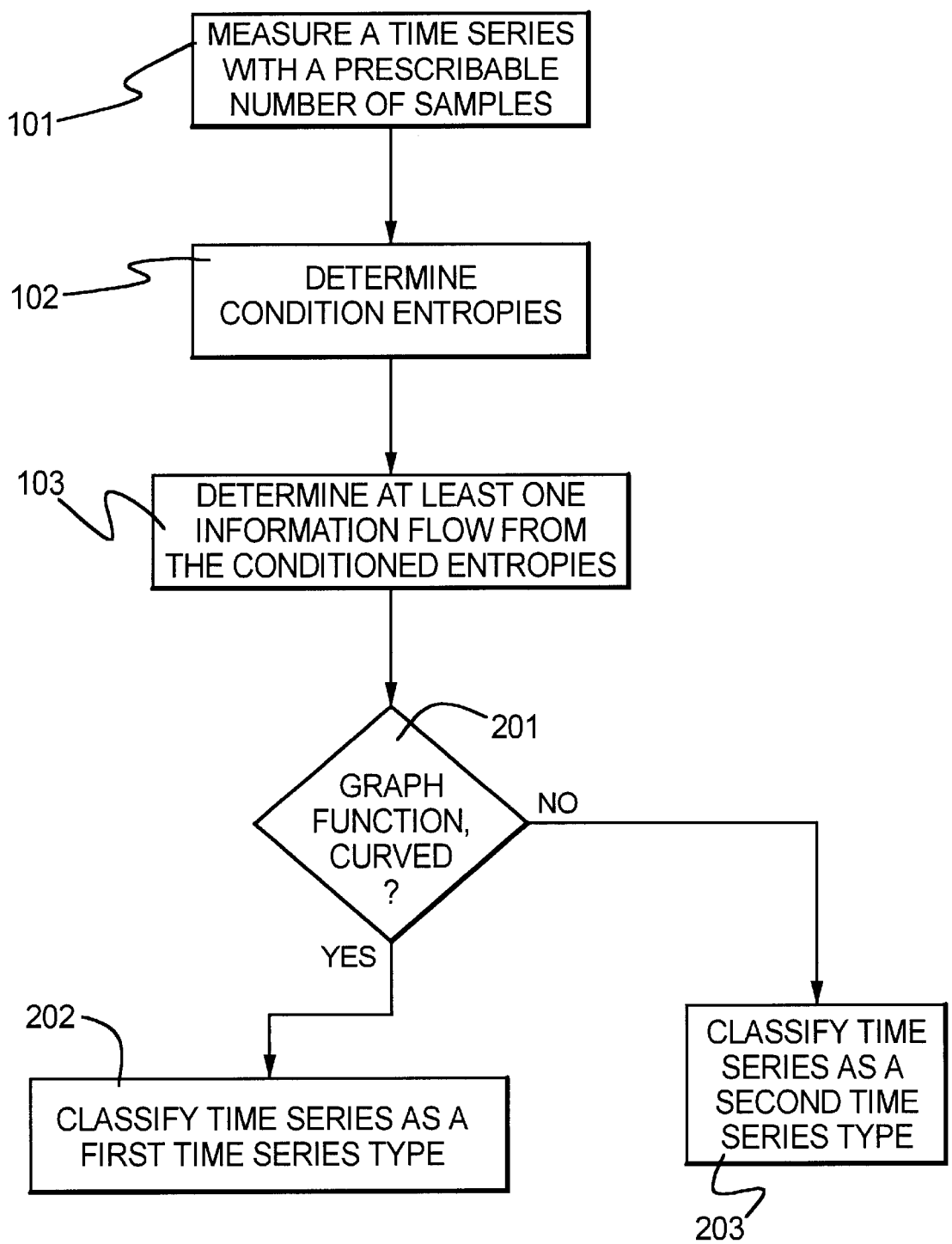
FIG. 2 is a flowchart showing a variation of the basic steps in FIG. 1.

On the basis of the graph of the information flow $I_p^\beta$ for future samples 201, a check is performed in a check step 202 to see whether the graph is, perhaps, curved or whether is steeply drops linearly (see FIG. 2).

When the shape of the graph exhibits a parabola-like, slightly curved, descending shape, then the time series is classified as the first time series type ZT1. Given a time series that is established by a measured cardiogram signal (ECG), this corresponds to a classification of the electrocardiogram signal (ECG) into an electrocardiogram signal (ECG) of a heart at risk with respect to sudden cardiac death.

When, however, the graph exhibits a steeply dropping, linear shape, then the time series is classified 203 into the second time series type ZT2. For the example of the electrocardiogram signal, this corresponds to the classification of the ECG signal as an ECG signal of a heart not at risk with respect to sudden cardiac death.

Figure 3:
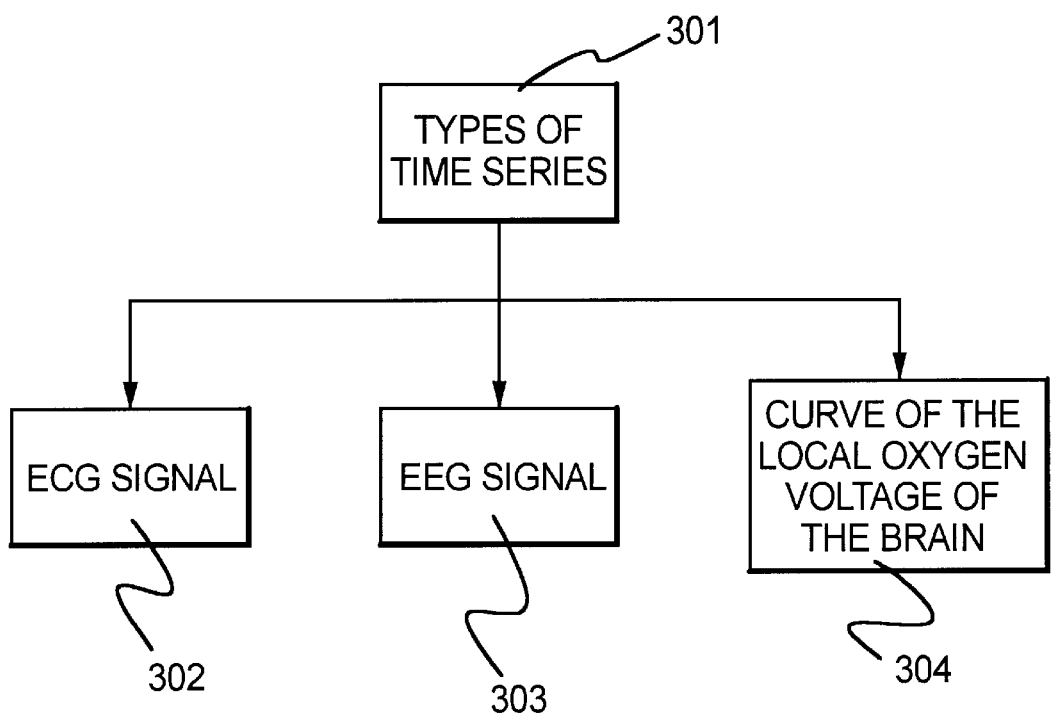
FIG. 3 is a block diagram illustrating classification of various possible time series in accordance with the invention.

FIG. 3 indicates 301 various possibilities for the types of a time series for which the method can be utilized. The invention is not, however, in any way limited to these examples. The method can be employed for any type of time series wherein it is important to determine non-linear correlations between the samples of the time series and to classify the time series on the basis of these non-linear correlations that are reflected in the information flow.

For example, the time series can be:

an electrocardiogram signal (EGG signal) 302;

an electroencephalogram signal (EEG signal) 303;

a signal that describes the curve of the oxygen voltage of a brain 304.

Figure 4:
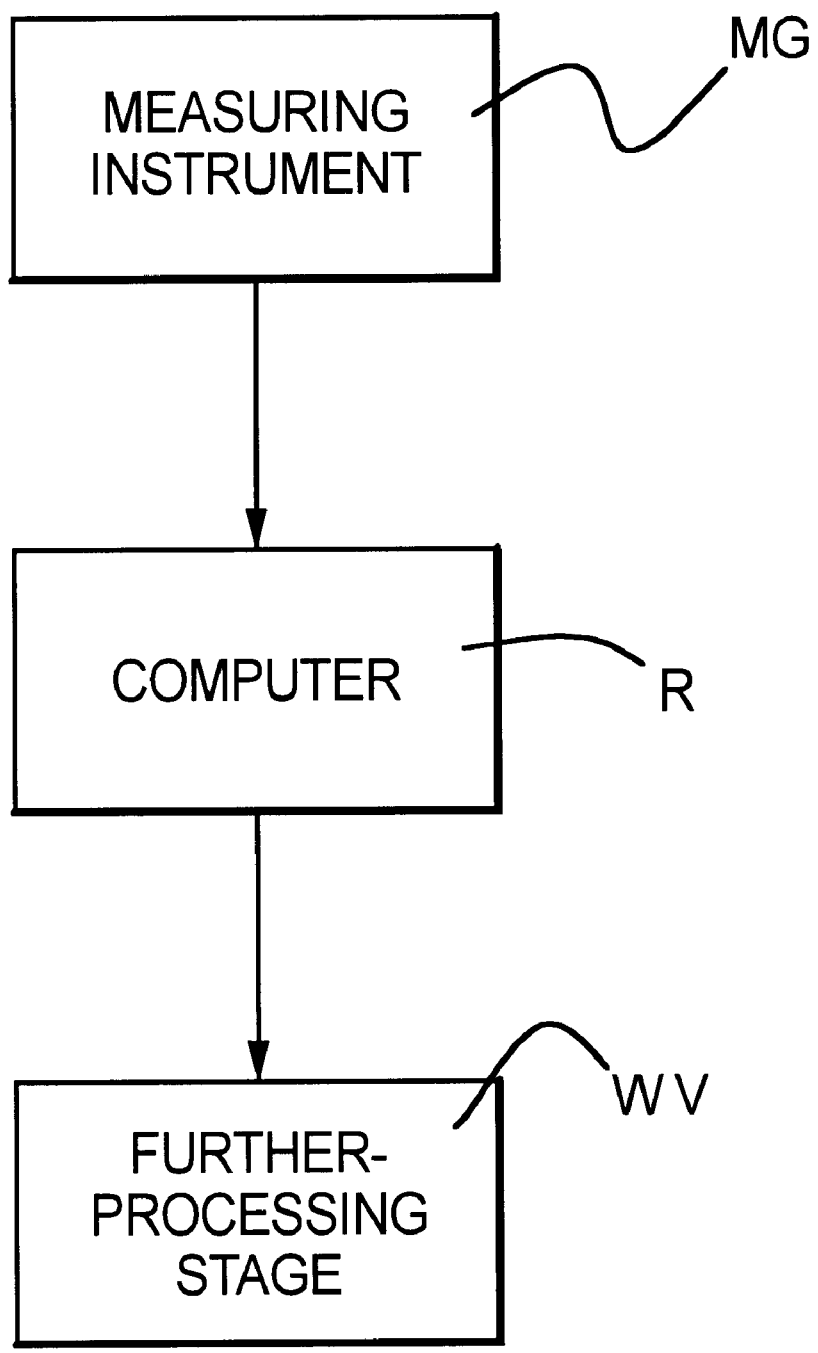
FIG. 4 is a block diagram showing the basic components of a computer for implementing the inventive method.

FIG. 4 shows the computer R with which the inventive method is necessarily implemented.

The computer R processes the time series registered by the measuring instrument MG and supplied to the computer R.

It is thereby of no significance whether the formation of the samples from the possibly analog signal is implemented in the measuring instrument MG or in the computer R. Both versions are provided for the inventive method.

The measuring instrument can, for example, be an electrocardiograph (ECG), an electroencephalograph (EEG) or an apparatus, too, that works according to the method presented in [2].

The classification result that was determined by the computer R in the above-described way is further-processed in a means for further-processing WV and, for example, is displayed for a user. This means WV can, for example, be a printer, a picture screen or a loudspeaker as well, via which an acoustic or visual signal is forwarded to a user.

Although modifications and changes may be suggested by those skilled in the art, it is the intention of the inventors to embody within the patent warranted hereon all changes and modifications as reasonably and properly come within the scope of their contribution to the art.

What is claimed is:

1. A method for classification of a time series, the method comprising:

gathering a prescribable plurality of samples of an electrical signal;

determining conditioned entropies relating to the samples;

determining at least one information flow for a prescribable plurality of future sampling times from the conditioned entropies; and determining a classification of the time series based upon the information flow.

2. The method of claim 1, wherein the step of determining conditioned entropies includes of determining all conditioned entropies of the samples of the time series.

3. The method of claim 2, wherein the step of determining the conditioned entropies includes using the rule:

$$H(n|n-1\ldots 1)=\Sigma_{i=1}^{k^{n-1}}\Sigma_{j=1}^{m}p(j,i)\cdot\log(p(j|1)),$$

whereby $H(n|n-1\ldots 1)$ references conditioned entropies, n references a length of a sequence of samples of the time series, $k_n$ ($k_n=m^n$) references a plurality of different sequences of samples having the length n, m references a plurality of values that the samples can assume, $p(j,i)$ references the union probabilities, and $p(j,|i)$ references conditioned probabilities.

4. The method of claim 3, wherein the step of determining at least one information flow includes using the rule, $$I^\beta(n+1;n+p|n\ldots 1)=H^\beta(n+p|n\ldots I)-H^\beta(n+p|n+1\ldots I),$$

whereby $\beta$ describes a partition with which a plurality m of values that the samples can assume is prescribed.

5. The method of claim 4, wherein the step of determining a classification of the time series includes classifying the time series into either a first time series type or into a second time series type.

6. The method of claim 5, further comprising establishing the time series by a measured electrocardiogram signal (EKG).

7. The method of claim 5, further comprising establishing the time series by a measured electroencephalogram signal (EEG).

8. The method of claim 5, further comprising establishing the time series by a measured signal that describes the voltage curve of a brain pressure.

* * * * *